United States Patent
Jones et al.

(10) Patent No.: US 11,234,628 B2
(45) Date of Patent: *Feb. 1, 2022

(54) NON-INVASIVE SYSTEMS AND METHODS TO DETECT CORTICAL SPREADING DEPRESSION FOR THE DETECTION AND ASSESSMENT OF BRAIN INJURY AND CONCUSSION

(71) Applicants: Stephen Carter Jones, Pittsburgh, PA (US); Prahlad Menon Gopalakrishna, Pittsburgh, PA (US); Alexander Kharlamov, Pittsburgh, PA (US); Philip M Sauter, Pittsburgh, PA (US); Nicolas A. Alba, Pittsburgh, PA (US); Samuel J. Hund, Pittsburgh, PA (US); Eric Singer, Pittsburgh, PA (US)

(72) Inventors: Stephen Carter Jones, Pittsburgh, PA (US); Prahlad Menon Gopalakrishna, Pittsburgh, PA (US); Alexander Kharlamov, Pittsburgh, PA (US); Philip M Sauter, Pittsburgh, PA (US); Nicolas A. Alba, Pittsburgh, PA (US); Samuel J. Hund, Pittsburgh, PA (US); Eric Singer, Pittsburgh, PA (US)

(73) Assignee: SCIENCEPLUSPLEASE, LLC, Pittsburgh, PA (US)

( * ) Notice: Subject to any disclaimer, the term of this patent is extended or adjusted under 35 U.S.C. 154(b) by 360 days.

This patent is subject to a terminal disclaimer.

(21) Appl. No.: 16/041,763

(22) Filed: Jul. 21, 2018

(65) Prior Publication Data
US 2019/0038167 A1 Feb. 7, 2019

Related U.S. Application Data

(63) Continuation-in-part of application No. 14/948,995, filed on Nov. 23, 2015, now Pat. No. 10,028,694.
(Continued)

(51) Int. Cl.
 *A61B 5/372* (2021.01)
 *A61B 5/00* (2006.01)
 (Continued)

(52) U.S. Cl.
 CPC ............ *A61B 5/291* (2021.01); *A61B 5/2415* (2021.01); *A61B 5/30* (2021.01); *A61B 5/316* (2021.01);
 (Continued)

(58) Field of Classification Search
 None
 See application file for complete search history.

(56) References Cited

U.S. PATENT DOCUMENTS 4,051,842 A * 10/1977 Hazel .................. A61B 5/0408 600/391
4,270,543 A * 6/1981 Tabuchi ............... A61B 5/0408 600/396
(Continued)

FOREIGN PATENT DOCUMENTS

WO WO-2016003966 A1 * 1/2016 .......... A61B 5/0476

OTHER PUBLICATIONS

Case, G. R., Cortical Spreading Depression in Classical Conditioning: Issues in Associated Cerebral and Cerebellar Eyeblink Circuitry; Dissertation presented to Faculty of the Graduate School of University of Southern California; Dec. 1999. (Year: 1999).*
(Continued)

*Primary Examiner* — Etsub D Berhanu
(74) *Attorney, Agent, or Firm* — Gwen R. Acker Wood; Acker Wood IP Law LLC

(57) ABSTRACT

The present invention provides systems and methods for detection and diagnosis of concussion and/or acute neurologic injury comprising a portable headwear-based electrode array and computerized control system to automatically and
(Continued)

accurately detect cortical spreading depression and acute neurological injury-based peri-infarct depolarization (CSD/PID). The portable headwear-based electrode system is applied to a patient or athlete, and is capable of performing an assessment automatically and with minimal user input. The user display indicates the presence of CSD/PID, gauges its severity and location, and stores the information for future use by medical professionals. The systems and methods of the invention use an instrumented DC-coupled electrode/amplifier array which performs real-time data analysis using unique algorithms to produce a voltage intensity-map revealing the temporally propagating wave depressed voltage across the scalp that originates from a CSD/PID on the brain surface.

3 Claims, 10 Drawing Sheets

Related U.S. Application Data

(60) Provisional application No. 62/084,247, filed on Nov. 25, 2014.

(51) Int. Cl.
*A61B 5/291* (2021.01)
*A61B 5/30* (2021.01)
*A61B 5/316* (2021.01)
*A61B 5/375* (2021.01)
*A61B 5/24* (2021.01)

(52) U.S. Cl.
CPC ............ *A61B 5/375* (2021.01); *A61B 5/4076* (2013.01); *A61B 5/6803* (2013.01); *A61B 2562/0215* (2017.08); *A61B 2562/046* (2013.01)

(56) References Cited

U.S. PATENT DOCUMENTS

| | | | | |
|---|---|---|---|---|
| 4,955,382 A * | | 9/1990 | Franz | A61B 5/042 600/375 |
| 5,348,006 A * | | 9/1994 | Tucker | A61B 5/0478 600/383 |
| 2003/0036696 A1* | | 2/2003 | Willis | A61B 5/6858 600/424 |
| 2004/0073127 A1* | | 4/2004 | Istvan | A61B 5/04087 600/513 |
| 2009/0326404 A1* | | 12/2009 | Sajda | G06K 9/0057 600/544 |
| 2010/0210963 A1* | | 8/2010 | Tonini | A61B 5/0484 600/544 |
| 2011/0015503 A1* | | 1/2011 | Joffe | A61B 5/0478 600/301 |
| 2012/0143020 A1* | | 6/2012 | Bordoley | A61B 5/1114 600/301 |
| 2014/0058528 A1* | | 2/2014 | Contreras-Vidal | A61B 5/0496 623/25 |
| 2014/0163408 A1* | | 6/2014 | Kocher | A61B 5/7275 600/544 |
| 2014/0303470 A1* | | 10/2014 | Tsukada | D06P 1/38 600/377 |
| 2016/0120432 A1* | | 5/2016 | Sridhar | A61B 5/4082 600/544 |
| 2016/0143574 A1* | | 5/2016 | Jones | A61B 5/04012 600/544 |

OTHER PUBLICATIONS

Fabricius et al. Cortical spreading depression and peri-infarct depolarization in acutely injured human cerebral cortex. Brain (2006), 129, 778-790. (Year: 2006).*

Drenckhahn et al. Correlates of spreading depolarization in human scalp electroencephalography. Brain 2012: 135; 853-868. (Year: 2012).*

* cited by examiner

FIG. 8A
FIG. 8B
FIG. 8C
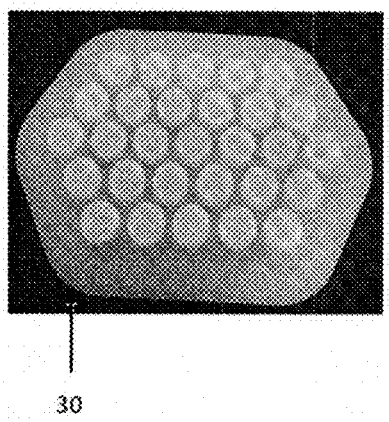
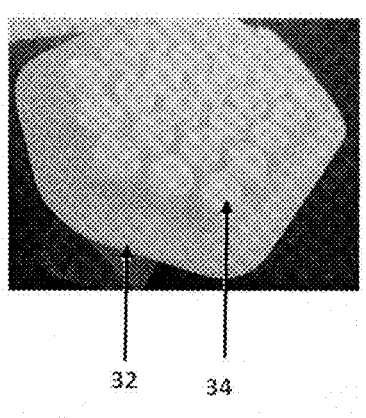
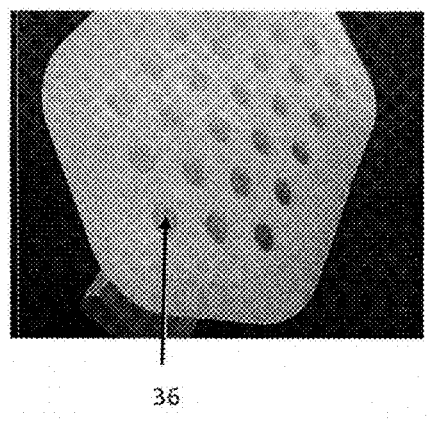
30
32   34
36

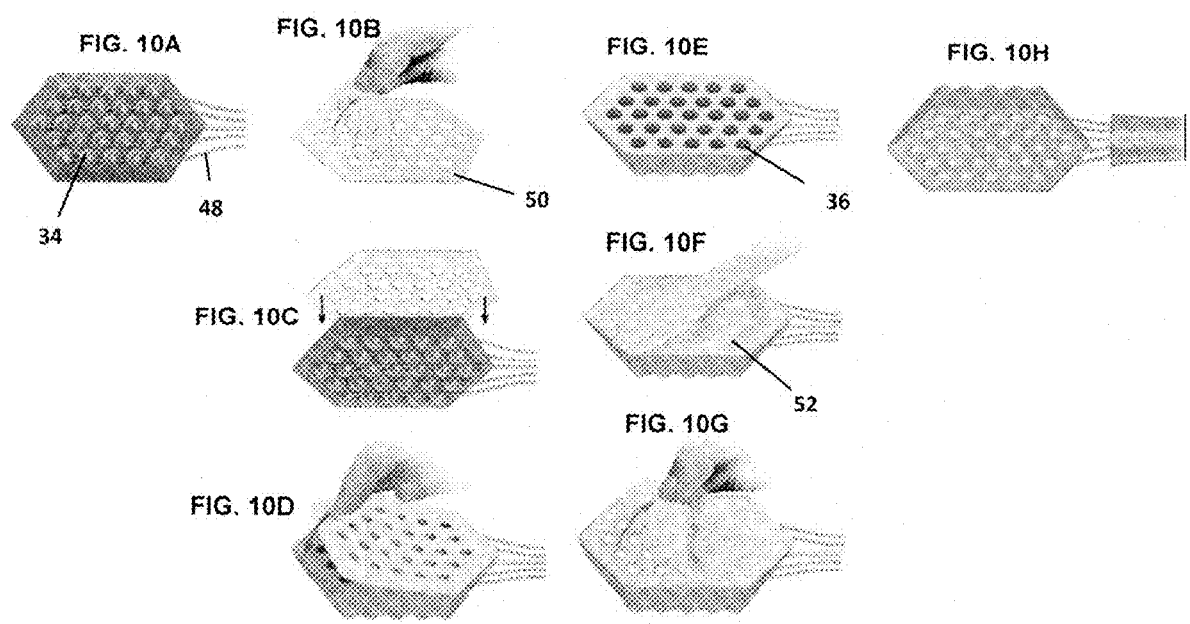

NON-INVASIVE SYSTEMS AND METHODS TO DETECT CORTICAL SPREADING DEPRESSION FOR THE DETECTION AND ASSESSMENT OF BRAIN INJURY AND CONCUSSION

CROSS REFERENCE TO RELATED APPLICATIONS

The present application claims priority to U.S. patent application Ser. No. 14/948,995, filed Nov. 23, 2015, which claims priority to U.S. Provisional Application No. 62/084,247, filed Nov. 25, 2014, both of which are incorporated in their entirety herein by reference.

FIELD OF THE INVENTION

The present invention relates to the field of detection and diagnosis of concussion and/or acute neurologic injury; to neurologic triage for acute ischemic stroke, traumatic brain injury, intracerebral hemorrhage, and subarachnoid hemorrhage; and to the evaluation of athletic-induced head injury; specifically, to an athletic field sideline-placed or portable apparatus using a computer-based method for performing emergency neurological triage on a subject who has recently suffered a blow to the head to determine if the subject is suffering from episodes of cortical spreading depression (CSD) associated with concussion; and specifically, to a neuro-intensive care unit- or emergency medicine setting-placed portable apparatus using a computer-based method for performing neurological triage on a subject who has recently suffered an acute neurologic injury to determine if the subject is suffering from episodes of cortical spreading depression (CSD).

BACKGROUND OF THE INVENTION

Mild traumatic brain injury (mTBI), commonly called concussion, has an annual incidence estimated as 130.8 per 100,000 in the United States. The economic impact of concussion is substantial, with annual U.S. estimates reaching $3 billion, and is increasing due to more sensitive diagnosis and increased awareness. Available data indicate that the total costs for mTBI, or concussion, are high, and that the indirect costs, such as for sick leave, early retirement and loss of productivity, are the main expense.

Stroke is the fourth leading cause of death in the United States and affects 6.8 million Americans (overall prevalence 2007-2010 was 2.8%). Almost 800,000 new strokes occur each year (approximately 23% are recurrent strokes). In 2009, strokes cost the U.S. economy $38.6 billion and the mean lifetime cost of ischemic stroke is $140,048. Traumatic brain injury, intracerebral hemorrhage, and subarachnoid hemorrhage have similar if not greater prevalence and impact statistics.

A review of CSD is helpful, as the concussion and neurological injury detection systems and methods described below is based on the properties and characteristics of CSD. CSDs and their initiation by mechanical stimulation of the brain surface were first reported in 1944, but were considered an experimental curiosity until their association with acute neurological injury and their identification as the phenomenology behind migraine auras. CSDs and their pathological correlate in ischemic brain regions, peri-infarct depolarizations (PIDs), are important phenomena related to stroke and other brain pathologies. Currently, CSDs and their neurophysiological and other properties are not detectable from the surface of the scalp by existing commercial methods and devices.

CSD is a cellular depolarization wave in cerebral gray matter involving both neurons and glia with a dimensional extent of from about 3 mm to about 6 mm, which is characterized by the depression of evoked and spontaneous electroencephalography (EEG) activity from the brain spreading at a rate of 1 to 9 mm/min across the cortical surface. The spontaneous EEG remains markedly depressed for ½ to 1 min, and then returns to normal within the following 5 to 10 min, whereas the evoked synaptic activity usually takes longer to recover (i.e., 15 to 30 min). CSD is characterized by a complete loss of neuronal activity, which can last for minutes, before complete recovery. Simultaneously, the local tissue potential (the DC potential) swings negative with amplitudes of 15 to 30 mV for 1 min or more. At the surface of the scalp, this DC potential is reduced to approximately 300 µV. The EEG depression coincides with and is caused by a dramatic failure of brain ionic homeostasis and near equalization of extra-, intra-, and total brain ionic concentrations: most notably, extracellular concentration of potassium, i.e., $[K^+]_{ex}$ increases from a normal of 3 mM to 30-60 mM. In summary, CSDs can be characterized as about 5 mm regions of cellular depolarization with high, approximately 60 mM $[K^+]_{ex}$, which travel at about 3 mm/min across the brain cortex with a DC potential of approximately –20 mV.

CSDs can be initiated experimentally by cortical pinprick, electrical stimulation, cortical application of $K^+$, or mechanical force to the cortex. Stroke PIDs, the pathological correlate of CSDs, occur in three temporal windows: 1) initial depolarization, which is fundamentally different than subsequent PIDs; 2) an acute stage of stroke (<6 h); and 3) a delayed late phase starting at 6-8 to 24 plus hours. A concussive CSD has similarities to the initial PID in ischemic stroke.

For many years, it was believed that CSD was an artifact produced in animal experiments and without significance for human neurological conditions, but its association with migraine aura and acute neurological injury has tempered this reservation.

CSD, with its properties of depressed voltage and velocity, occurs in concussion and migraine aura without morphological brain tissue damage. CSD also occurs in acute neurological injury, including ischemic stroke, severe traumatic brain injury, intracerebral hemorrhage, and sub-arachnoid hemorrhage, where it is strongly associated with the expansion of morphologically observed brain damage.

Current techniques to observe CSDs in humans require exposure of the brain surface and the placement of electrode strips, an invasive procedure termed electrocorticography (ECoG). For example, Hartings et al. (Ann. Neurol., 2014, 76:681) disclose first identifying depolarizations in ECoG recordings, then examining scalp EEG correlates. Drenckhahn et al. (Brain, 2012, 135:853) disclose observing limited regions of depressed voltage with scalp EEG associated with underlying CSDs identified with ECoG, but not the detection of a spread of slow potential change or AC-EEG depression of spontaneous activity between different scalp electrodes. Ayaz et al. (Am. J. Emerg. Med., 2015, 33:493) disclose a device that uses discriminative analysis of multiple quantitative EEG parameters from a five electrode forehead electrode array, assesses the effects of concussion on generalized neurotransmission abnormalities that are not specific to concussion, but is not sensitive to the characteristics of CSD. Nowhere in the prior art, therefore, are there disclosures to fully detect propagating CSDs noninvasively from the surface of the scalp.

The detection and diagnosis of concussion has been problematic for several reasons. Most of the acute methods, implemented soon after a concussion, are based on psychometric testing, balance assessment, or subtle eye movements. None of these methods is able to directly detect or quantify the neurological basis of concussion, and instead are performed to detect secondary indicators that can be ambiguous and inconsistent in nature. Imaging via MRI, CT, PET, ultrasound, or near-infrared spectroscopy also is not compatible with observing CSD in the setting of concussion.

There is intense interest and need for systems and methods to detect and evaluate acute sports or injury-related concussions. Post-concussion detection schemes, which are starkly distinguishable from the present invention, include ImPACT, a psychometric test that compares a pre-athletic measurement with a measurement on the sidelines for post-concussion evaluation. Although it has become the de facto standard, it is also acknowledged to be imprecise and ineffectual.

None of the prior methods or devices utilizes CSD as an indicator of concussion, which is described in more detail in the embodiments of the present invention described below.

SUMMARY OF THE INVENTION

The present invention provides systems and methods to detect concussion-based cortical spreading depression (CSD) and acute neurological injury-based peri-infarct depolarization (PID) in a subject, using a finely spaced DC-compatible electrode array, DC-capable amplifiers, and post-processing algorithms implemented by one or more processors which implement programming instructions.

In an aspect of the invention, there is provided a method of detecting concussion-based cortical spreading depression (CSD) in a subject. This method is implemented by one or more processors implementing programming instructions and comprises: receiving from a detection unit comprising a plurality of scalp electrodes configured as a high density electrode array spaced between about 0.5 cm and about 1.5 cm apart from one another, a set of electrical potential signals from a brain area of a patient; determining that values of a first set of the electronic potential signals corresponding to a first portion of the brain area, representing a CSD, are depressed as compared to values of a second set of the electronic potential signals corresponding to a second portion of the brain area, representing normal brain; and generating an output in response to the determining step, said output indicating that the patient is experiencing a concussion-based CSD.

This method further comprises: receiving a ground voltage from a ground electrode which is in contact with a non-brain area of the patient; using the received ground voltage to determine the primary DC voltage, $V_i$, for each of the plurality of scalp electrodes; using the primary DC voltage, $V_i$, to calculate a derived virtual ground voltage ($V_g$) for the plurality of scalp electrodes; determining a derived electrode voltage ($V_{ig}$) based on the mean of the derived virtual ground voltages ($V_g$) for each of the scalp electrodes; determining whether the derived electrode voltages indicates a depression in a voltage level among a set of adjacent electrodes; and outputting a report indicating a level of the depression and the area to which the depression corresponds.

In another aspect of the invention, there is provided a system for detecting concussion-based cortical spreading depression (CSD) in a patient. The system is implemented by one or more processors implementing programming instructions and comprises: a detection unit comprising a plurality of scalp electrodes configured as a high density electrode array, said plurality of scalp electrodes spaced between about 0.5 cm and about 1.5 cm apart from one another and configured to detect electrical potential signals when placed on a scalp area of a patient; an amplifier unit configured to amplify the detected electrical potential signals; and a processing unit comprising one or more processors and a non-transitory computer-readable memory containing programming instructions that, when executed, causes the processing unit to receive the amplified signals and determine, for each received signal whether the signal corresponds to an electrode placed above a normal cortex area of the patient or above an ischemic cortex area of the patient; determine whether the electrode voltages indicate a depression in a voltage level among a set of adjacent electrodes in one of the areas, and if so, determine whether the depression corresponds to electrodes above the normal cortex area or above the cortex area representing a CSD; and output a report indicating a level of the depression and the area to which the depression corresponds.

This system further comprises: a ground electrode configured to detect a ground voltage when placed on a non-scalp area of the patient, and additional programming instructions that, when executed, cause the processing unit to use the detected ground voltage to determine a mean derived normal area ground voltage ($V_g$); determine a derived electrode voltage ($V_{ig}$) based on the mean derived normal area ground voltage ($V_g$) for each of the received signals corresponding to the normal cortex area; and use the derived electrode voltages when determining whether the electrode voltages indicate a depression in a voltage level.

In another aspect of the invention, there is provided a method of detecting an acute neurological injury-based cortical spreading depression and peri-infarct depolarization (CSD/PID) in a subject. The method is implemented by one or more processors implementing programming instructions and comprises: receiving from a detection unit comprising a plurality of scalp electrodes configured as a high density electrode array spaced between about 0.5 cm and about 1.5 cm apart from one another, a set of electrical potential signals from a brain area of a patient; determining that values of a first set of the electronic potential signals corresponding to a first portion of the brain area, representing a CSD/PID, are depressed as compared to values of a second and third set of the electronic potential signals corresponding to a second portion of brain area, representing ischemic brain, and third portion, representing normal brain; and generating an output in response to the determining step, said output indicating that the patient is experiencing an acute neurological injury-based CSD/PID.

This method further comprises: receiving a ground voltage from a ground electrode that is in a contact region above a non-brain area of the patient; performing a data collection process for each of the electrodes above a brain area, said data collection process comprising determining an initial voltage, $V_i$, in reference to the ground voltage of the ground; sequentially dividing these voltages into two groups; determining mean values of each of these two groups; comparing, for each sequential determination of the two mean voltages, their difference; choosing among these two groups, the largest difference; choosing the electrode voltages of the group with the lowest mean voltage to be termed, $V_{ig\text{-}ischemic}$; choosing the electrode voltages of the group with the highest mean voltage to be termed, $V_{ig\text{-}normal}$; using this initial voltage, $V_{ig\text{-}normal}$, to derive a virtual ground voltage for electrodes above the normal cortex area ($V_{gm\text{-}normal}$), and using the virtual ground voltage for electrodes above the normal cortex area ($V_{gm\text{-}normal}$) and the initial voltage, $V_{ig\text{-}normal}$, to derive a normal area virtual voltage for each electrode classed as being above a normal brain area ($V_{ig}$); using the initial voltage, $V_{ig\text{-}ischemic}$, to derive a virtual ground voltage for electrodes above the ischemic cortex area ($V_{gm\text{-}ischemic}$), and using the virtual ground voltage for electrodes above the ischemic cortex area ($V_{gm\text{-}ischemic}$) and the initial voltage, $V_{ig\text{-}ischemic}$, to derive an ischemic area virtual voltage for each electrode originating above an ischemic area ($V_{ig}$); combining the two sets of $V_{ig}$ values to indicate a depression in a voltage level among a set of adjacent electrodes that corresponds to a CSD/PID; repeating the data collection process for a plurality of epochs and using results of the data collection to determine whether a depression of voltage level travels at a velocity that is consistent with cortical spreading depression (CSD)/PID characteristics; determining that the depression corresponds to electrodes within a region above the acute neurological injury-based CSD/PID when it is determined that the depression of voltage level travels at a velocity that is consistent with CSD/PID characteristics; generating an output indicating that the patient is experiencing the acute neurological injury-based CSD/PID; and outputting a report indicating a level of the depression corresponding to the CSD/PID and the area to which the depression corresponds.

In another aspect of the invention, there is provided a system for detecting an acute neurological injury-based cortical spreading depression and peri-infarct depolarization (CSD/PID) in a patient. The system is implemented by one or more processors implementing programming instructions and comprises: a detection unit comprising a plurality of scalp electrodes configured as a high density electrode array, said plurality of scalp electrodes spaced between about 0.5 cm and about 1.5 cm apart from one another and configured to detect electrical potential signals when placed on a scalp area of a patient; an amplifier unit configured to amplify the detected electrical potential signals; and a processing unit comprising one or more processors and a non-transitory computer-readable memory containing programming instructions that, when executed, causes the processing unit to receive the amplified signals and determine, for each received signal whether the signal corresponds to an electrode placed above a normal cortex area of the patient or above an ischemic cortex area of the patient or above an area of cortex that represents a CSD/PID; determine whether the electrode voltages indicate a depression in a voltage level among a set of adjacent electrodes above one of the areas, and if so, determine whether the depression corresponds to electrodes above the normal cortex area or above the ischemic cortex area or above an area of cortex that represents a CSD/PID; and output a report indicating a level of the depression and the area to which the depression corresponds.

This system further comprises: a ground electrode configured to detect a ground voltage when placed on a non-scalp area of the patient, and additional programming instructions that, when executed, cause the processing unit to use the detected ground voltage to determine a mean derived normal area ground voltage ($V_{g\text{-}normal}$) and a mean derived ischemic area ground voltage ($V_{g\text{-}ischemic}$); determine a derived electrode voltage ($V_{ig}$) based on the mean derived normal area ground voltage ($V_{gm\text{-}normal}$) for each of the received signals corresponding to the normal cortex area; determine a derived electrode voltage ($V_{ig}$) based on the mean derived ischemic area ground voltages ($V_{gm\text{-}ischemic}$) for each of the received signals corresponding to the ischemic cortex area; and use the derived electrode voltages, $V_{ig}$, when determining whether the electrode voltages indicate a depression in a voltage level.

In an embodiment of the systems and methods of the invention, the plurality of scalp electrodes is spaced about 1.0 cm apart from one another.

In accordance with the systems and methods of the invention, a velocity of propagation between 1.0 mm/min and 9.0 mm/min is consistent with CSD and PID characteristics.

In accordance with the systems and methods of the invention, the detection unit determines severity, morphology, velocity of propagation and trajectory of the CSD-based concussion and the acute neurological injury-based PID, the severity proportional to the magnitude of DC voltage depression and area over which the DC voltage depression occurs, the morphology exhibited as a globular, expanding ring, and the trajectory comprising an initiation point, an extinguish point, and a branching pattern.

The systems and methods of the present invention utilize the unique characteristics of the DC properties of CSDs, including the voltage and volume of their propagation, to implement their detection. The systems and methods of the present invention in various embodiments uses a High Density Electrode Array which is placed on the head of the test subject, DC-coupled electroencephalography amplifiers, post-processing algorithms and software, and a user interface that provide a unique solution to non-invasive CSD detection.

Various embodiments of these systems and methods, utilizing post-processed DC-potentials obtained from finely-spaced multi-electrode arrays, fill the missing link between the complimentary needs for a concussion detection method and for monitoring CSDs in acute neurological injury and the available technologies by providing a simple method of data processing, based on detection of CSDs and their pathological correlate, PIDs, in the brain. CSDs propagate across the brain at slow velocity (1 to 9 mm/min in normal brain tissue). CSDs are a primary pathophysiological basis of concussion and are associated with increased brain damage and brain cell death in acute neurological injury. The systems and methods described herein implement a scheme for the non-invasive detection of concussion- and neurological injury-based CSDs from the surface of the scalp.

The embodiments of the present invention are useful for sports and injury-related concussion and acute neurological injury diagnosis as applied to, for example, both amateur and professional athletes and the general population who suffer strokes, severe traumatic brain injury from vehicle and other accidents, intracerebral hemorrhage, and sub-arachnoid hemorrhage. The systems and methods have applicability in emergency medical care, law enforcement, military, and industrial environments.

The systems and methods of the present invention are embodied by a portable, instrumented head-mounted unit, which includes a High Density Electrode Array, combined with a Signal Acquisition System, a Detection Algorithm System, and a Display and Output Module which detects CSD associated with concussion and acute neurological injury and gauges its severity. An advantage of such technology is that it allows for the reduction or elimination of the complex and often inaccurate process of concussion diagnosis and treatment based on symptomatology that is presently the standard of care and that it allows the non-invasive observation of brain-damaging CSDs/PIDs in acute neurological injury.

Prior method for concussion detection and diagnosis are not based on the observation or detection of the primary neurological consequences of a blow to the head. Prior method for monitoring acute neurological injury are not based on the mass neural and glial depolarization that initially and later characterizes acute neurological injury. The embodiments of the present invention consider a moving wave of CSD: 1) to be a principal indicator of concussion; and 2) which is consistently present at both the acute and later stages of acute neurological injury. The systems and methods of the present invention are based on the detection of these primary neurological events associated with concussion and acute neurological injury, instead of secondary, more ambiguous and inconsistent indicators such as cognitive or movement deficits or eye movement abnormalities. No prior method, device, or system possesses this inherent focus on CSD as a main player in concussion and acute neurological injury.

BRIEF DESCRIPTION OF THE DRAWINGS

A fuller understanding of the invention can be gained from the following description when read in conjunction with the following drawings.

FIG. 4A-C show the results of a numerical simulation with the result that the electrode spacing of 1.0 cm allows accurate reconstruction of the CSD structure from scalp detection, in accordance with an embodiment of the present invention, in which FIG. 4A shows the estimated true scalp voltage intensity map at 10 min after CSD initiation; FIG. 4B shows the scalp voltage intensity accurately reconstructed from a 1.0 cm electrode array; and FIG. 4C shows the voltage intensity scale with black representing both 0 mV and −2 mV.

FIG. 5A-B are design drawings of the High Density Electrode Array, in which FIG. 5A is a front and side plan view of the 1.0 cm electrode spacing, and FIG. 5B is a perspective view of the 1.0 cm electrode spacing, used in conjunction with a DC-coupled amplifier to detect CSDs on the scalp, in accordance with an embodiment of the present invention.

FIG. 8A-C are pictures of the scaffold, in which FIG. 8A is a top view; FIG. 8B is a top isometric view; and FIG. 8C is a bottom isometric view.

FIG. 10A-H are illustrations of the high density electrode array, referred to as the CerebroPatch CSD Detection Array, and adhesive strip, referred to as CerebroAttach Adhesive Strip, in which FIG. 10A shows the CerebroPatch with electrode domes facing up and wire harness on the right; FIG. 10B shows the adhesive strip with paper backing being removed; FIG. 10C shows the CerebroPatch and the adhesive strip facing down; FIG. 10D shows the matching of the outline of the adhesive strip the CerebroPatch; FIG. 10E shows the CerebroPatch face up; FIG. 10F shows smearing conductive paste using a sterile tongue depressor onto the exposed face of the adhesive strip; FIG. 10G shows the removal of the remainder of the paper backing; and FIG. 10H shows the CerebroPatch with conductive paste-filled electrodes.

DETAILED DESCRIPTION OF THE INVENTION

Definitions

Figure 1:
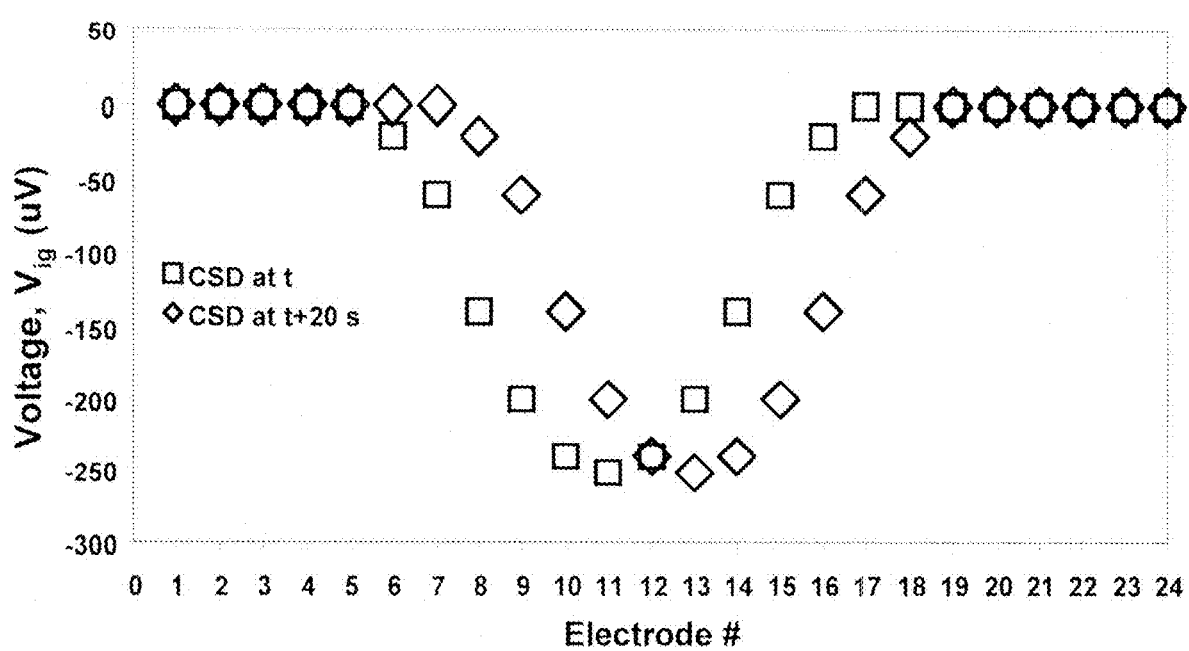
FIG. 1 shows the results of an averaging scheme by displaying the scalp DC voltage after post-processing of a concussion- or acute neurological injury-induced CSD at two sequential times using a one-dimensional electrode array model, in accordance with an embodiment of the present invention. DC-potential measurements are plotted at each scalp electrode for the CSD detection scheme showing two sequential measurements separated by 20 sec. The vertical axis displays the post-processed DC voltage, $V_{ig}$, from the noise-reducing averaging scheme.

As used in this document:
The terms "cortical spreading depression" and "peri-infarct depolarization" are phenomena which are meant to be interchangeable.
$[K^+]_{ex}$=extracellular potassium concentration
CSD=cortical spreading depression
CT=computed tomography
EEG=AC-coupled electroencephalography
ECoG=electrocorticography
DC-coupled-EEG=DC-coupled electroencephalography
PET=positron emission tomography
TBI=traumatic brain injury
mTBI=mild traumatic brain injury
PIDs=peri-infarct depolarizations
MRI=magnetic resonance imaging
Vg=derived virtual ground voltage
Vg-ischemic=derived virtual ground voltage of ischemic cortex
Vg-normal=derived virtual ground voltage of normal cortex
Vi=initial electrode DC voltage
Vig=derived electrode voltage
Vig-ischemic=derived electrode voltage for ischemic cortex electrodes
Vig-normal=derived electrode voltage for normal cortex electrodes
Vgm-ischemic=mean electrode voltage for ischemic cortex
Vgm-normal=mean electrode voltage for normal cortex The need for concussion detection systems and methods that quickly, consistently, and reliably work is enormous, given the current publicity which currently surrounds concussion: newspaper articles, TV spots, and parental concern for young athletes. Sports-related concussion is an important and emerging health care issue, with enormous increasingly recognized impact on our children and adult athletes. Additionally, there is enormous need for a simple, reliable, and portable concussion detection systems and methods in many other situations, including law enforcement, military, construction, industry, and emergency care. Current methods for the testing of the effects of concussion are not effective, as they are slow, complicated, inaccurate, or inconsistent.

Embodiments of the systems and methods of the present invention provide both the detection and the gauging of severity immediately following a concussion event, a potentially invaluable addition to current practices in the art. The systems and methods of the present invention help mitigate the economic impact of delayed treatment with the immediate knowledge of the severity and occurrence of a concussion.

The need for a non-invasive CSD detection system for acute neurological injury is expressed repeatedly by those who currently use invasive electrocorticography method for its detection in the setting of the neurological intensive care unit. The systems and methods of the present invention for the non-invasive monitoring of brain-damaging CSDs/PIDs permit the investigation of brain-saving pharmaceutical and physiological stratagems in over twenty times the number of patients who are not candidates for medically mandated craniotomies, a procedure that is necessary for the placement of electrodes on the brain surface needed for ECoG recording procedures. The systems and methods of the present invention help mitigate the economic impact of further brain damage with the immediate knowledge of the severity and occurrence of CSDs.

CSDs can be initiated experimentally by cortical pin-prick, electrical stimulation, cortical application of $K^+$, or mechanical force to the cortex. The mechanical shock to the brain that precedes a concussion produces the same effect, a CSD. The present invention provides the surprising finding of a connection between concussion and CSDs which heretofore has been relatively unknown by those skilled in the art.

In the prior art, propagating CSDs have been impossible to detect noninvasively from the surface of the scalp. Although propagating CSDs have been successfully detected on the brain surface, the system and method described in the embodiments of the present invention can detect CSDs on the scalp using DC-coupled-EEG combined with a post-processing averaging scheme to mitigate DC drift and noise.

The present invention includes systems and methods that detect CSDs non-invasively from the surface of the scalp. Given the current understanding that CSDs are pathogenic and occur in virtually every form of acute neurological injury, the systems and methods of the present invention can be deployed non-invasively in a variety of situations, such as in the neuro-intensive care unit and at the emergency medical technician level. Embodiments of the systems and methods can be used, for example: 1) by sports medicine professionals, within any sport with concussion risk and at all levels of professional and amateur play; 2) in emergency medicine; and 3) in the neuro-intensive care unit. The systems and methods are fully portable and adaptable for ambulance, emergency room, and critical care use, as well as to sites where a concussion injury risk is present, such as construction and heavy industry.

In various embodiments, the systems and methods of the present invention include a real-time scalp DC-potential data collection system which detects a CSD using electrode/amplifier/data transmission/post-processing/visual display technology. The systems and methods of the present invention are able to identify the presence of concussion and the pathological progression of acute neurological injury via the presentation of CSDs—centers of low voltage which propagate across the brain as waves of depolarization in cerebral gray matter—in real-time voltage intensity-map images of low-pass filtered scalp-potentials detected with DC-coupled-EEG.

The systems and methods of the present invention include, without limitation, five or more components, described below and shown visually in the drawings. These five or more components include both a physical apparatus and software.

The components of the systems and methods of the present invention include a high density electrode array incorporated into a head-net which fits inside a helmet, a stand-alone head-net, a head-band, a grid, or other electrode positioning unit which detects and transmits real-time scalp DC-potentials to a laptop/workstation or a computer which amplifies and evaluates the recordings to detect concussion and CSD/PID events and gauges their severity. The system includes a detection scheme that is based on the relationship between CSD and both concussion and acute neurological injury, and involves the detection of slowly moving (at 1 to 9 mm/min)−10 to −45 mV DC-potentials from the brain surface through the scalp using a 1.0 cm spaced active High Density Electrode Array and sensitive DC-coupled amplifiers.

The components of the systems and methods of the present invention can gauge the severity of concussion and CSDs present in acute neurological injury by evaluating and recording a combination of the level of the depressed voltage that is a characteristic of CSD, the surface area on the scalp in which this depressed voltage resides, the velocity of the propagating CSD wave, the morphology and shape of the depressed voltage, and the propagation trajectory (e.g. initiation point, extinguish point, branching pattern) of the detected CSD wave.

The rapid and reliable detection of CSD associated with concussion and following acute neurological injury is a critically important and potentially life-changing need in emergency health care, athletics, and the intensive care unit. The systems and methods of the present invention includes a portable headwear-based electrode array and computerized control system capable of automatically and accurately detecting CSD associated with acute neurological injury and concussion events following blows to the head. The systems and methods can be easily applied to the patient or athlete by minimally-trained medical technicians, and can perform a diagnosis automatically and with minimal user input and does not require a base-line, pre-concussion, or pre-injury test.

The systems and methods of the present invention are a fully portable system which includes an array of scalp surface electrodes, the High Density Electrode Array, coupled with a computerized control unit with integrated signal amplifier. The High Density Electrode Array is incorporated into an elastic head-net or band or flexible grid for easy, rapid, and comfortable application and removal from a patient. Following application of the High Density Electrode Array to the patient, the control unit electrically assesses electrode placement and proper skin contact, and performs an automated diagnostic procedure by analyzing scalp electrical potentials to detect tell-tale signs of acute neurological injury or concussion. This portable system requires as little input from the medical technician as possible, and causes minimal discomfort to the injured patient. A user display indicates the presence of CSD as a positive indication of concussion and is used to detect CSD and PID presence, velocity, shape, trajectory, and location as evidence of severity, and the system stores the information in a non-transitory, computer-readable memory for future use by medical professionals.

The system of the present invention implements a diagnostic procedure to detect DC-potential changes resulting from mechanical shock-induced CSD induced by concussion and from CSDs associated with acute neurological injury, using an instrumented DC-coupled electrode/amplifier array that performs real-time data analysis using novel and unique algorithms. These algorithms produce a voltage intensity-map image revealing the temporally propagating DC potential wave (which originates from the surface of the brain cortex) across the scalp surface. This voltage intensity map is displayed as an image on a computing device screen as a color-coded image of the propagating DC-potential propagating over a representation of the scalp. The system uses CSD as an important pathophysiological trait of acute neurological injury and concussion. CSD typically has been considered to be very difficult to detect on the scalp surface, as it manifests as a DC potential change well below the frequency range recorded using established EEG methodology, and whose spatial extend is not compatible with current clinical EEG configurations. The system of the present invention includes proven DC-coupled-EEG method to overcome this limitation through the use of high spatial density electrodes, a custom-configured amplification system, post-processing algorithms, and visual display units. Through this methodology, the systems and methods of the present invention can be deployed to detect CSDs associated with concussion, stroke, intracerebral hemorrhage, traumatic brain injury, intracerebral hemorrhage, and sub-arachnoid hemorrhage.

Referring now to FIG. 1, the results of an averaging scheme are shown by displaying the scalp DC voltage after post-processing of a concussion- or acute neurological injury-induced CSD at two sequential times using a one-dimensional electrode array model for a clear description of the detection scheme. In this scheme, DC-noise and drift is mitigated by an averaging scheme that establishes a derived virtual ground. This derived virtual ground is then subtracted from each electrode voltage and further processed using temporal and spatial weighted averaging schemes to obtain post-processed DC voltage $V_{ig}$ for each electrode. The vertical axis displays $V_{ig}$ from this noise- and drift-reducing averaging scheme. This voltage is plotted at each scalp electrode for the CSD detection scheme showing two sequential measurements separated by 20 seconds.

Figure 2:
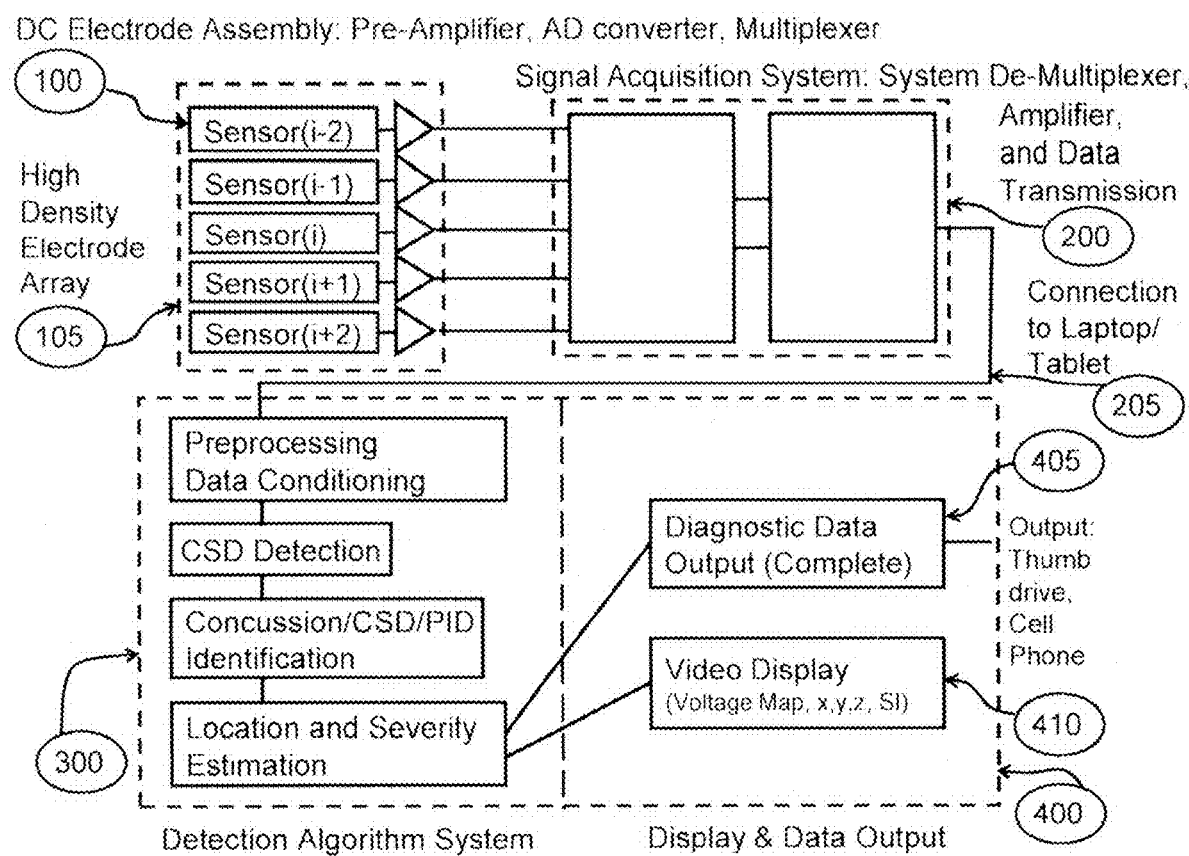
FIG. 2 is a block diagram showing components of the system, in accordance with an embodiment of the present invention.

The systems and methods can include as many as five or more core elements. As shown in FIG. 2, a block diagram bringing together various components of an embodiment of the system includes: 1) the DC Electrode Assembly, a plurality of DC-EEG electrodes composed of a cylinder filled with cotton soaked with electrode gel or water, a sintered Ag/AgCl electrode, a preamplifier, an analog-to-digital converter, and multiplexer that is associated with each electrode 100; 2) the detection unit, which includes a High Density Electrode Array, a helmet/headband/grid-based DC-EEG High Density Electrode Array assembly composed of a plurality of closely-spaced DC-Electrode Assemblies 105; 3) a Signal Acquisition System that includes a de-multiplexer, amplifier, and a cable or wireless data transmission system 200 that provides a connection to a computing device 205; 4) a laptop- or tablet-based Detection Algorithm System that includes a Preprocessing Data Conditioning module, a CSD Detection system, a Concussion/CSD/PID Identification system, and a Location and Severity Estimation system 300; and 5) a display and data output/presentation system 400 that includes a Diagnostic Data Output module that displays textual diagnostic information and outputs to a computer-readable memory such as a USB thumb drive or a mobile electronic device such as a cell phone 405 and a Video Display screen 410 that shows a voltage intensity-map of the scalp surface over which the wave of negative DC potential passes from a propagating CSD on the brain surface.

Figure 3:
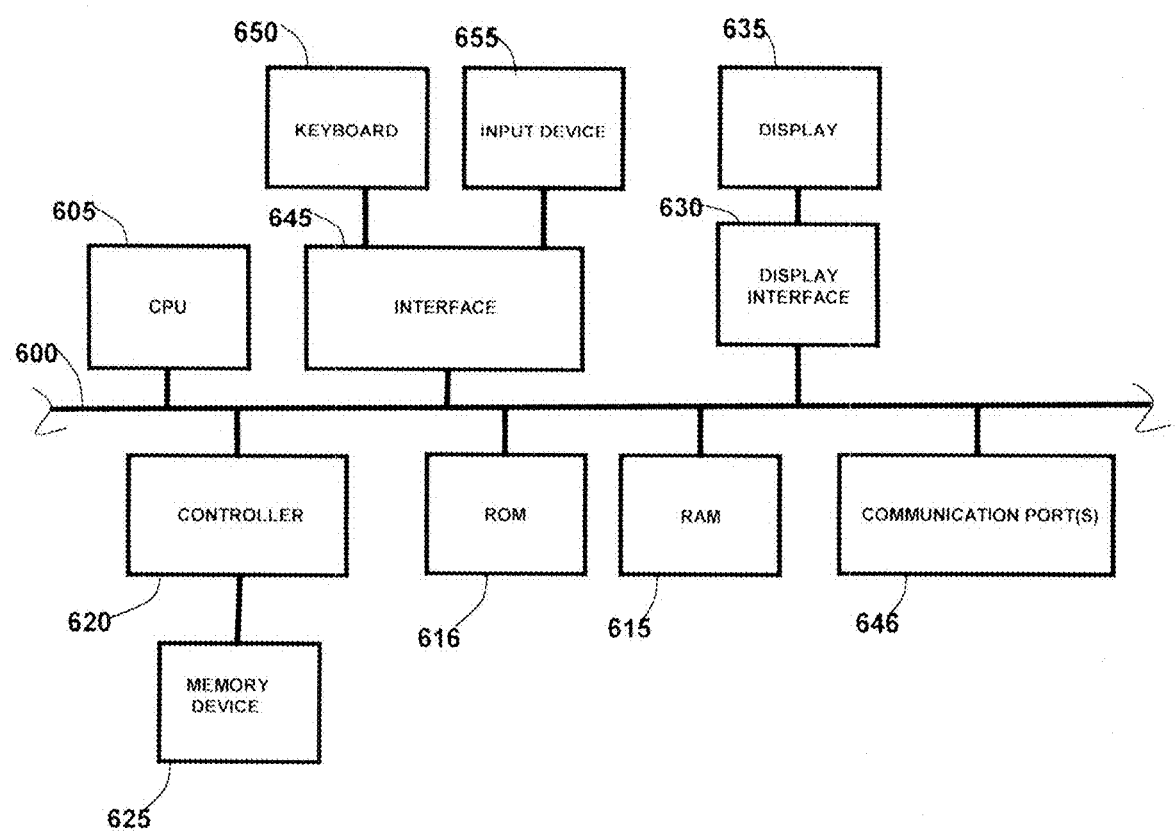
FIG. 3 shows internal hardware used to contain or implement the various automated processing elements, in accordance with an embodiment of the present invention.

FIG. 3 shows internal hardware that is used to contain or implement the various automated processing elements of the present invention. An electrical bus 600 serves as an information highway interconnecting the other illustrated components of the hardware. CPU 605 is a central processing unit of the system, performing calculations and logic operations required to execute a program. CPU 605, alone or in conjunction with one or more of the other elements disclosed in FIG. 3, is a processing device, computing device or processor. Read only memory (ROM) 610 and random access memory (RAM) 615 are examples of memory devices employed in implementing the systems and methods of the present invention.

A controller 620 interfaces with one or more optional memory devices 625 that serve as data storage facilities to the system bus 600. These memory devices 625 may include, for example and without limitation, an external DVD drive or CD ROM drive, a hard drive, flash memory, a USB drive or another type of device that serves as a data storage facility. As indicated previously, these various drives and controllers are optional devices. Additionally, the memory devices 625 can be configured to include individual files for storing any software modules or instructions, auxiliary data, incident data, common files for storing groups of contingency tables and/or regression models, or one or more databases for storing the information as discussed above.

Program instructions, software or interactive modules for performing any of the functional steps associated with the processes as described above may be stored in the ROM 610 and/or the RAM 615. Optionally, the program instructions may be stored on a tangible computer readable medium such as a compact disk, a digital disk, flash memory, a memory card, a USB drive, an optical disc storage medium and/or other recording media.

A display interface 630 permits information from the bus 600 to be displayed on the display 635 in audio, visual, graphic or alphanumeric format. Communication with external devices occurs using various communication ports 640. A communication port 640 is attached to a communications network, such as the Internet, a local area network or a cellular telephone data network.

The hardware also includes an interface 645 which allows for receipt of data from input devices such as a keyboard 650 or other input device 655 such as a remote control, a pointing device, a video input device and/or an audio input device.

Figure 4A:
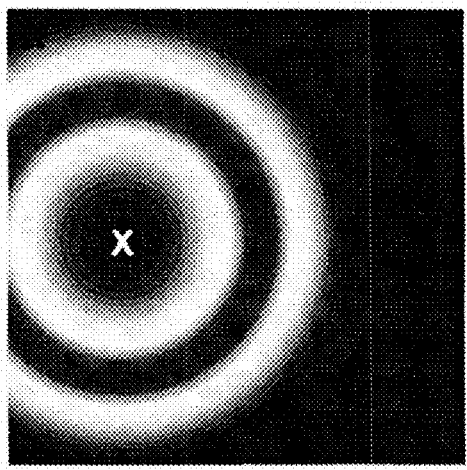
Figure 4B:
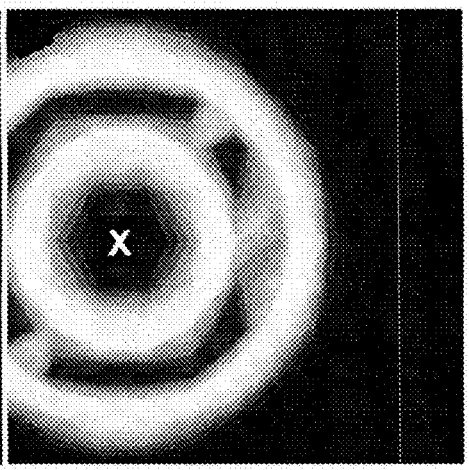
Figure 4C:
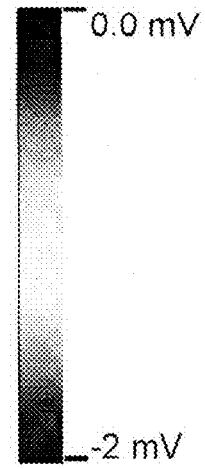

FIG. 4 shows the results of a numerical simulation with the result that the electrode spacing of 1.0 cm allows accurate reconstruction of CSD structure from scalp detection. FIG. 4A shows the estimated true scalp voltage intensity map at 10 min after CSD initiation in a 10 cm×10 cm simulation domain. The symbol "X" marks the focal point of the CSD on the underlying brain surface. FIG. 4B shows the scalp voltage intensity reconstructed from a 1.0 cm-spaced electrode array. FIG. 4C shows the voltage intensity scale with black representing both 0 mV and −2 mV. Zero mV values are apparent at both the focal point of the CSD and completely outside the ring. Minus 2 mV values and other values are present within the ring structure. These scalp voltages represent about 8% of the voltage on the brain surface used in this simulation. This modeling and simulation approach is utilized to determine the optimum number and spatial distribution of sensors required to detect a CSD-based concussion and an acute neurological injury-based PID, while minimizing noise. The model can use previous data, such as data of PIDs detected from a model of ischemic stroke from both laser speckle flowmetry and fast apparent diffusion coefficient magnetic resonance imaging.

Figure 5A:
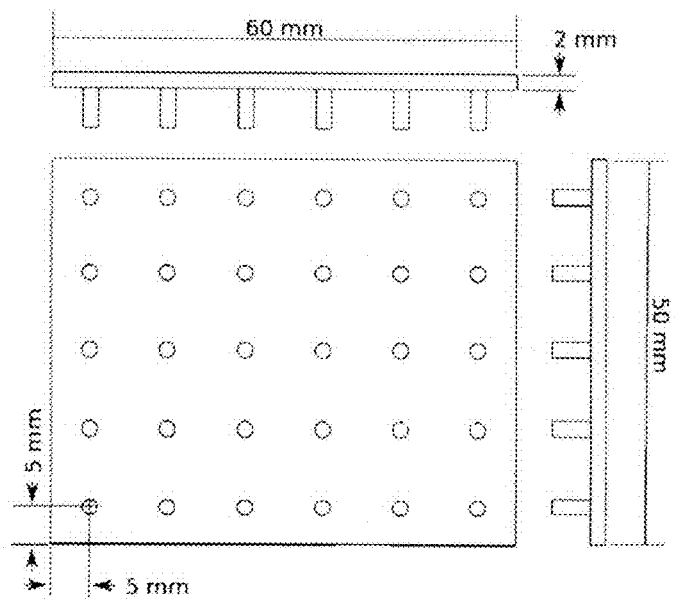
Figure 5B:
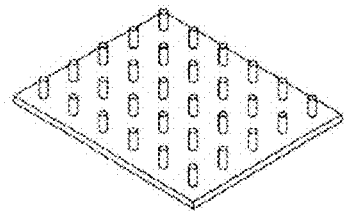

FIG. 5 shows the High Density Electrode Array that is used in conjunction with a DC-coupled amplifier to detect CSD on the scalp of the individual. FIG. 5A shows orthogonal views (edge, top, and side) of the High Density Electrode Array. FIG. 5B shows the configuration of the High Density Electrode Array. The detection of CSDs from a concussion and from acute neurological injury is based on the mathematical simulation of the scalp detection of a CSD using the High Density Electrode Array with 1.0 cm spacing described above, and the averaging scheme for eliminating noise and drift. All electrodes are placed 1.0 cm apart: center-to-center, with each electrode having a 2.0 mm diameter.

Figure 6:
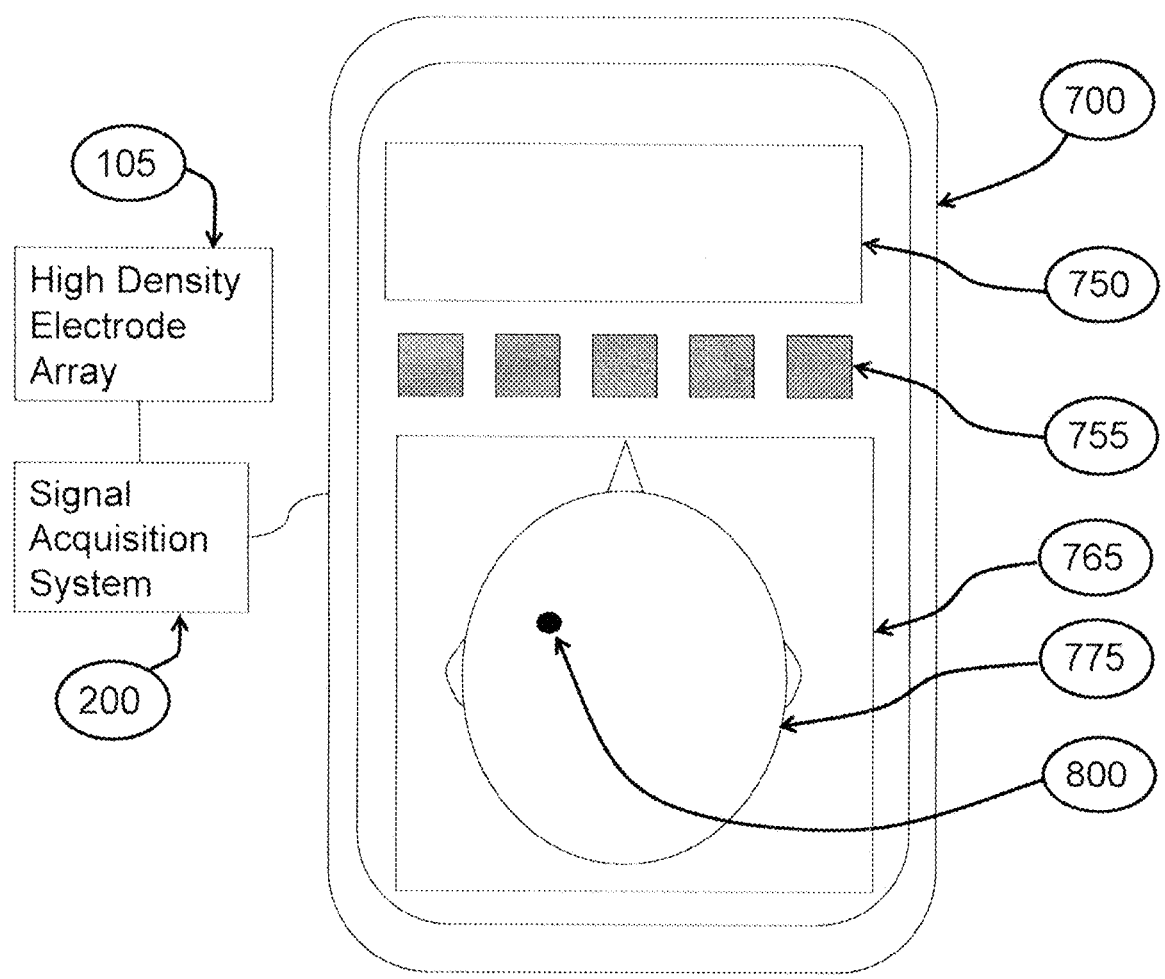
FIG. 6 is a diagrammatic representation of the Detection Algorithm System and the Display and Data Output module, in accordance with an embodiment of the present invention.

FIG. 6 is a diagrammatic representation of the computing device 700 combining the Detection Algorithm System 300 and the Display and Date Output 400 shown in FIG. 2 which includes components to detect the presence of the CSD, the severity of the CSD, morphology of the particular CSD (e.g. globular, expanding ring), velocity of CSD propagation, and trajectory of CSD propagation (e.g. initiation point, extinguish point, branching pattern) in the individual: 1) screen for informational text including diagnostic data output 750; control buttons 775; video display 750 which shows a diagrammatic representation of the individual's scalp 775; the voltage intensity map of depressed voltage that identifies the CSD 800; the High Density Electrode Array 105; and Signal Acquisition System 200 shown in FIG. 2.

Detection of CSDs and PIDs (CSD/PID)

Two schemes are used for the detection of CSDs, one scheme for the detection of concussion, and the other scheme for the detection of CSDs/PIDs in acute neurological injury.

Detection of CSDs from Concussion

A scheme for the detection of CSDs from concussion is based on post-processing with a different reference scheme and increased electrode array spacing compared to standard EEG practice. This detection scheme is based on DC potentials detected from a finely spaced multi-electrode array. The DC potential of each electrode in the array is obtained repetitively every 10 to 30 seconds, or at other suitable intervals. The DC potential of a single electrode is referenced to a derived virtual ground voltage obtained by summation of all the other DC potentials and further processed with weighed-averaging schemes. A CSD is detected if this processed signal shows a negative value that moves with the appropriate velocity consistent with known CSD properties across the electrode array. Depending on the electrode spacing, several electrodes within or near an area of about 4 mm diameter, the area of a depolarization wave, should show a similar negative signal.

A one-dimensional array of electrodes composed of electrodes $E_1, \ldots, E_i, \ldots, E_n$ placed on the scalp, is used to describe this detection scheme. Every 10 to 30 seconds, or at other suitable $$Vg = \frac{\sum_{i=1}^{n} Vi}{n}$$

intervals, the DC voltage from each of these electrodes is determined as $V_i$ in reference to an Ag/AgCl ground electrode placed on the skin of the neck. A derived virtual ground voltage, Vg, is calculated as:

and a derived electrode voltage, $V_{ig}$, is calculated as:

$$V_{ig} = V_i - V_g.$$

A plot of these $V_{ig}$'s is shown in FIG. 1. The depression between $V_i$ and $V_{i+7}$ shows the position of a CSD. A new calculation of $V_{ig}$ is performed every 10 to 30 seconds, or at other suitable intervals.

In another embodiment of the present invention for detecting CSDs from concussion, these derived virtual ground averaging schemes can also use weighted averaging over: 1) a limited number of 10 to 30 second (or other suitable) collection epochs; and 2) a limited number of electrodes rather than a greater number of electrodes.

The Detection of CSDs from Acute Neurological Injury

A scheme for the detection of CSDs from acute neurological injury including ischemic stroke, traumatic brain injury and sub-arachnoid hemorrhage, is based on post-processing with a different reference scheme and increased electrode array spacing compared to standard EEG practice. This detection scheme is based on DC potentials detected from a finely spaced multi-electrode array. The DC potential of each electrode in the array is obtained repetitively every 10 to 30 seconds, or at other suitable intervals. The DC potential of a single electrode is referenced to a derived virtual ground voltage obtained by summation of all the other DC potentials and further processed with weighed-averaging schemes. A CSD is detected if this processed signal shows a negative value that moves with the appropriate velocity across the electrode array. Depending on the electrode spacing, several electrodes within or near an area of about 4 mm diameter, the area of a depolarization wave, should show a similar negative signal.

A one-dimensional array of electrodes composed of electrodes $E_1, \ldots, E_i, \ldots, E_n$ placed on the scalp, is used to describe this detection scheme (FIG. 1). Every 10 to 30 seconds, or at other suitable intervals, the DC voltage from each of these electrodes is determined as $V_i$ in reference to an Ag/AgCl ground electrode placed on the skin of the neck of a patient. A derived virtual ground voltage is calculated as described below.

This CSD/PID detection scheme for acute neurological injury includes the effect that the $V_I$ differ according to whether they originate from normal or ischemic cortex. This situation is implemented by a computation scheme that sequentially separates all the electrodes into two groups, chosen from all the possible divisions of contiguous electrodes (n−1 divisions in the one-dimensional model and $n^2$−1 for the electrode grid). Separate mean $V_g$'s, $V_{g\text{-}ischemic}$ and $V_{g\text{-}normal}$, are calculated for each grouping. The final grouping used for the calculation of the new derived virtual ground voltages, one for ischemic cortex and one for normal cortex, is chosen based on the widest difference between the $V_{g\text{-}ischemic}$ and $V_{g\text{-}normal}$. The voltages at the electrodes in these two groups are termed $V_{ig\text{-}ischemic}$ and $V_{ig\text{-}normal}$. The mean derived virtual ground voltages for the ischemic and normal cortex electrode groups, $V_{gm\text{-}ischemic}$ and $V_{gm\text{-}normal}$, are calculated from the averages using the number of electrodes in each $V_{gm\text{-}ischemic}$ and $V_{gm\text{-}normal}$ groups as the divisor, $$V_{gm\text{-}ischemic} = \frac{\sum_{i=1}^{n_{ischemic}} V_{ig\text{-}ischemic}}{n_{ischemic}}$$

-continued $$V_{gm\text{-}normal} = \frac{\sum_{i=1}^{n_{normal}} V_{ig\text{-}normal}}{n_{normal}}$$

The derived electrode voltages, $V_{ig}$, are calculated as:

$$V_{ig} = V_{ig\text{-}ischemic} \times V_{gm\text{-}ischemic} \text{ or } V_{ig} = V_{ig\text{-}normal} \times V_{gm\text{-}normal}.$$

A plot of these $V_{ig}$'s is shown in FIG. 1. The depression between $V_{ig}$ and $V_{(i+7)g}$ shows the position of a CSD, as shown by the plot of $V_{ig}$ at t+20 s. A new calculation of $V_{ig}$ is performed every 10 to 30 seconds, or at other suitable intervals.

In another embodiment of the present invention for detecting CSDs from acute neurological injury, these derived virtual ground averaging schemes can also use weighted averaging over: 1) a limited number of 10 to 30 second (or other suitable) collection epochs; and 2) a limited number of electrodes rather than a greater number of electrodes.

Detection Algorithm

The size/area, velocity, shape, and location (center of mass) of the CSD is determined using processed DC voltages from each electrode. Averaging over time also is exploited with boundaries at approximately 20 data acquisition epochs of 10 to 30 seconds before and after a suspected CSD. This average is subtracted from all epochs, so that the CSD will be apparent. This is followed by threshold segmentation. Finally, cluster tracking for automatic identification of contiguous and moving values of diminished DC voltage is implemented. This approach identifies regions of diminished DC voltage with the crucial criteria that the velocity of the identified object must travel with known CSD velocities of 1-9 mm/min. As described above, the algorithm uses filters and temporo-spatial averaging for background subtraction based on the weighted least-square method, taking advantage of the array density. The weights are calculated combining the method of Kriging and objective interpolation. The reference potential, against which the active electrode voltages are compared, is obtained by averaging across all signals for each sample point. The algorithm explores the spatial derivatives as a tool of accentuating the leading edge of the CSD wave using the spatial LaPlacian. Machine learning methods are used to train a machine learning classifier for CSD detection parameters of optimal electrode offset and critical voltage initially using numerical simulation-based disease-specific models for a range of simulated CSD motion paths and then updated with training based on acquired CSD data.

The embodiments of the systems and methods of the present invention eliminate the complex and seemingly inaccurate process of concussion diagnosis based on symptomatology that presently is the state of the art in amateur and professional athletics and provides increased diagnostic capabilities for acute neurological injury. There is no similar technology that involves the recognition that CSDs are a property of concussion and acute neurological injury that can be detected from processed DC-potentials from a finely spaced scalp electrode grid.

EXAMPLES

The present invention is more particularly described in the following non-limiting examples, which are intended to be illustrative only, as numerous modifications and variations therein will be apparent to those skilled in the art.

The first four examples are prophetic examples of the embodiments of the present, which includes: 1) an instrumented electrode cap fitted under a helmet that transmits data to a sideline laptop or other computing device for data analysis; 2) an electrode head-net or head-band at the sidelines associated with a laptop or other computing device for analysis; 3) an electrode head-net, head-band, or grid in a neuro-intensive care unit for traumatic brain injury, acute ischemic stroke, intracerebral hemorrhage, and subarachnoid hemorrhage associated with a laptop for analysis; and 4) an electrode head-net or head-band in an emergency medical transport unit for traumatic brain injury, acute ischemic stroke, intracerebral hemorrhage, and subarachnoid hemorrhage associated with a laptop or other computing device for analysis.

Example 1—Instrumented Electrode Helmet Transmitting Data to a Sideline Laptop for Analysis In this example, a football player wearing a helmet instrumented with an electrode array cap that includes a High Density Electrode Array that transmits DC-coupled-EEG data to the sidelines is hit by another player on the right upper temporal aspect of the player's head. The player falls to the ground and is unable to get up. Data transmitted from the helmet cap to the sideline analysis system composed of the portable processing unit with visual display then is assessed. The system begins the analysis and identification procedure, while at the same time a doctor logs the standard concussion assessment questions and patient history into system. The system continues its performance for about thirty minutes, at which time the system provides information that the player has suffered a concussion by displaying a region of depressed voltage of about 200 V on a diagrammatic representation of the player's head in the form of an expanding ring with a width of about 3.0 mm that originates at the right temporal aspect of the player's head and expands at a velocity of about 3 mm/min, which is characteristic of cortical spreading depression (CSD). Thus, within a period of approximately 30 minutes after a suspected concussion, and when either on or being removed from the field, an electrode head unit, which includes a High Density Electrode Array, contained in the player's helmet, allows for the recording and processing of DC-coupled-EEG data of the player. At the sidelines, data is received by a data processing system comprised of a computing device. The data is transformed to a voltage intensity-map showing the location and propagation of a wave of CSD as a visually distinct ring-shaped region traveling across a representation of the scalp surface of the player.

Example 2—Electrode Cap at the Sidelines Associated with a Laptop for Analysis

In this example, a football player is hit by another player on the right upper temporal aspect of the player's head. The player falls to the ground and is unable to get up. The player is assisted off the field and placed on the sidelines. A portable headband/electrode net and processing unit with visual display is fastened onto the player's head and a button is clicked to start the software for the analysis and identification procedure of the condition of the player. At the same time, a doctor logs the standard concussion assessment questions and patient history into system. The system continues its performance for about thirty minutes, at which time the system provides information that the player has suffered a concussion by displaying a region of depressed voltage of about 200 V on a diagrammatic representation of the player's head in the form of an expanding ring with a width of about 3.0 mm that originates at the right temporal aspect of the player's head and expands at a velocity of about 3 mm/min, which is characteristic of a CSD. Thus, within a period of approximately 30 minutes after a suspected concussion, an electrode head unit, which includes a High Density Electrode Array, is placed on the player at the sidelines after an injury, allows for the recording and processing of DC-coupled-EEG data of the player. Data is received by a data processing system comprised of a computing device. The data is transformed to a voltage intensity-map showing the location and propagation of a wave of CSD as a visually distinct ring-shaped region traveling across a representation of the scalp surface of the player.

Example 3—Electrode Cap in a Neuro-Intensive Care Unit for Traumatic Brain Injury, Acute Ischemic Stroke, Intracerebral Hemorrhage, and Subarachnoid Hemorrhage Associated with a Laptop for Analysis In this example, a patient in the neuro-intensive care unit is monitored with an electrode head unit which includes a High Density Electrode Array for the presence of CSDs and PIDs using DC-coupled-EEG data and the processing scheme as described above in Examples 1 and 2. A health care practitioner places the electrode head unit on the patient's head over the border between normal undamaged brain and the suspected region of brain damage as deduced from imaging or a neurological exam. The electrode unit is connected to the processing and display unit via wireless or wired connections. Over a period of up to seven days, the system collects data consisting of globular regions of about 3.0 mm diameter of depressed voltage of about 200 µV which travel along the border of the suspected region of damaged brain and propagate at a velocity of approximately 3.0 mm/min in various trajectories including branching into two globular regions, disappearing into a sulcus and not reappearing, disappearing into a sulcus and then reappearing on the adjacent gyrus, propagating into regions of normal or damaged brain and extinguishing themselves, all of which are characteristic of a CSD/PID. These CSD/PID events are stored in memory and reviewed by the medical personnel as indications of an ongoing process which causes more brain damage. In addition, therapies are investigated to mitigate and diminish the frequency and occurrence of the observed CSDs/PIDs.

Example 4—Electrode Cap in an Emergency Medical Transport Unit for Traumatic Brain Injury, Acute Ischemic Stroke, Intracerebral Hemorrhage, and Subarachnoid Hemorrhage Associated with a Laptop for Analysis In this example, a patient in an emergency medical transport unit is monitored with an electrode head unit which includes a High Density Electrode Array for the presence of CSDs and PIDs using DC-coupled-EEG data and the processing scheme as described above in Examples 1 and 2. Emergency medical personnel place the electrode head unit on the patient's head. The electrode unit is connected to the processing and display unit via wireless or wired connections. During the journey to the medical facility, the system collects data consisting of globular regions of about 3.0 mm width or diameter of depressed voltage of about 200 V which travel along the border of the suspected region of damaged brain and propagate at a velocity of approximately 3 mm/min in various trajectories including branching into two globular regions, disappearing into a sulcus and not reappearing, disappearing into a sulcus and then reappearing on the adjacent gyrus, propagating into regions of normal or damaged brain and extinguishing themselves, all of which are characteristic of a CSD/PID. These CSD/PID events are stored in memory and reviewed by the medical personnel as indications of an ongoing process that causes more brain damage. In addition, therapies are investigated to mitigate and diminish the frequency and occurrence of the observed CSDs/PIDs.

Example 5—Electrode Design

I. Electrodes

Figure 7:
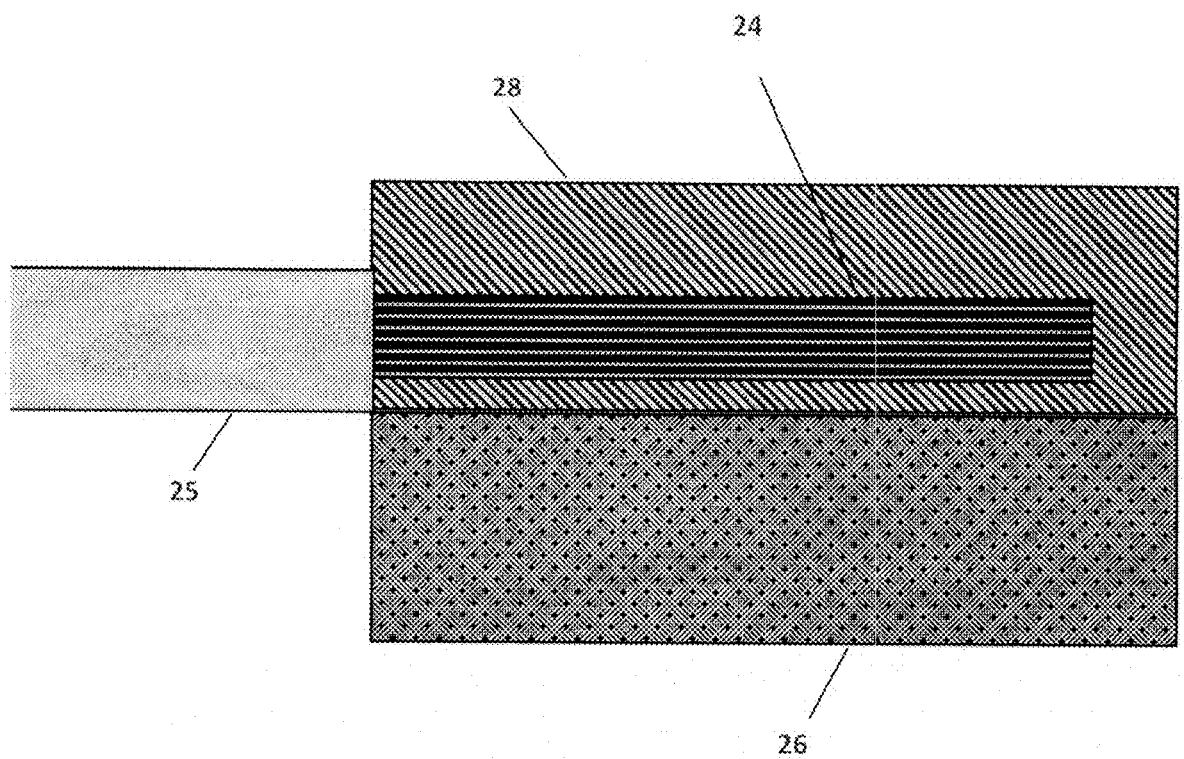
FIG. 7 is a side view of the electrode design in accordance with an embodiment of the present invention.

Different electrodes were contemplated for use in the present invention. For example, an electrode was considered with simply a short silver wire embedded in a silver/silver chloride (Ag/AgCl) electrode with a stripped portion of an insulated wire soldered to the electrode and encased in an epoxy. For this type, the short silver wire or insulated wire would break very easily. This type of electrode connection had a large amount of noise and collected lower quality data. As shown in FIG. 7, the inventors created a new electrode connection system in which a stripped portion 24 of an insulated wire 25 is attached to a sintered Ag/AgCl disk electrode 26 and then encased all at once using silver epoxy 28.

II. Scaffold

The scaffold used in the present invention includes several key new features, including having a thin and flexible webbing, a one cm spacing, and an electrode holder. The device is designed to be placed directly on a patient's skin using a double-sided adhesive tape and the electrode configuration is modified to a triangular configuration. As shown in FIG. 8, the key new features include: (1) a "rounded edge" 30 (FIG. 8A; top, overhead view) which decreases the likelihood of the device being accidentally peeled off; (2) a "tapered edge" 32 (FIG. 8B; top, isometric view) which makes the device more flexible, less likely to peel up, and easier to tape down; (3) an electrode holder 34; and (4) an electrode gel reservoir 36 included as part of the scaffold (FIG. 8C; bottom, isometric view).

III. Dome Cutaway

Figure 9:
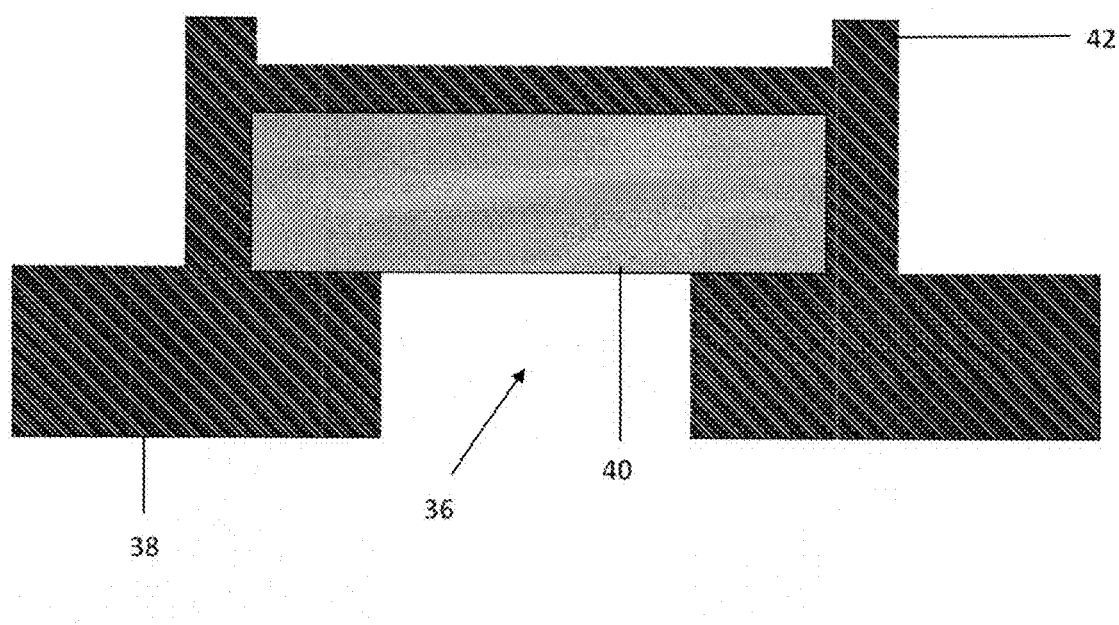
FIG. 9 is a front plan view of a cutaway of the dome design of the electrode dome in accordance with an embodiment of the present invention.

FIG. 9 shows a cutaway of the dome design to emphasize two key features of the electrode dome: (1) a "lip" 38 which holds the sintered Ag/AgCl electrode assembly 40 to make manufacturing more consistent, to protect the patient from the surface, and to prevent gel from being pushed out during placement of the device on the patient; and (2) a "dome ring" 42 which distributes the downward force (when the user presses the device onto a patient's scalp) directly through the scaffold to the scalp and not to the electrode gel reservoir 36.

Example 6—ANSYS Electronic Desktop in the Design of the CerebroPatch

I. Introduction

The inventors founded CerebroScope with the goal of saving brain cells. The inventors have developed a modified EEG system, called the CerebroPatch, with the goal of detecting, from the scalp, a CSD electrical signal in the brain that occurs after severe acute brain injury, such as stroke, subarachnoid and intracerebral hemorrhage, and severe traumatic brain injury. CSD increases energy consumption near the damage site, which can result in the death of compromised brain tissue.

The behavior of the electrical signal is well defined on the surface of the brain, but little data have been collected on the signal at the scalp. Obtaining this data would be financially prohibitive. Material and geometric parameters for biological tissues can vary greatly—up to three orders of magnitude—depending on where on the scalp the measurement is taken. These parameters also vary from patient to patient. The design challenge was to develop a prototype device for detecting these brain signals from the scalp as efficiently as possible.

II. Engineering Solution

The ANSYS Electronics Desktop allowed the inventors to mimic the complex, time-dependent electrical signal that occurs in the brain, and to simulate how it propagates through the layers from the brain surface to the scalp. The parametric capabilities allowed the inventors to study a wide variety of material parameters and geometric thicknesses. Coupled with Python scripting, the inventors easily generated output files and coupled them with real full-band EEG data to create artificial test cases. ANSYS' multiprocessor capabilities allowed the inventors to run simulations quickly and effectively.

III. Benefits

Using ANSYS Electronics Desktop allowed the inventors to obtain the spatiotemporal dynamics of a CSD's voltage potential on the scalp. The inventors quickly developed a robust, optimized device with signal processing software for clinical testing in less than one year, increasing the likelihood of success over the competition. ANSYS reduced design time by seventy-five percent compared to experimental methods, so clinical trials could start sooner.

CerebroScope's mission was to design, build and validate non-invasive devices for monitoring brain-damaging electrical signals referred to as CSDs.

Example 7—Instructions for Use of CerebroScope CerebroPatch CSD Detection Array

I. Description

The CerebroPatch CSD Detection Array by CerebroScope is a set of three components: (1) the CerebroPatch which makes contact with a patient; (2) the Amp-Side Cable; and (3) the CerebroAttach for attaching the CerebroPatch to the patient. The CerebroPatch CSD Detection Array serves to conduct electrical signals from the scalp to a full band EEG amplifier. An intermediate connector, between the Amp-Side Cable and the CerebroPatch, is positioned bedside to simplify connection and disconnection of the patient from the amplifier.

II. Indications for Use

The CerebroScope CerebroPatch is intended for use as a diagnostic tool for detecting and assessing CSD in patients diagnosed as having suffered an ischemic stroke, subarachnoid hemorrhage, intracranial hemorrhage, severe traumatic brain injury, mild traumatic brain injury, or migraine.

III. Contraindications

The CerebroScope CerebroPatch must not be used in an MRI environment; and must not be placed over open wounds or sutures.

IV. Warnings

1. The CerebroScope CerebroPatch diagnostic array must not be used if the patient has an allergy to silver (Ag), silver chloride (AgCl), sintered Ag/AgCl, thermoplastic elastomers or acrylate adhesives.

2. Direct skin contact must not be made with the electrodes. Contact with Ag/AgCl can cause localized permanent blue-gray discoloration of the skin discoloration that is called argyria.

3. The CerebroScope CerebroPatch must not be used for any other purpose than its intended use, for instance as a patch to hold skin or objects together. If cut and used as a patch, the CerebroScope CerebroPatch may lack adequate transverse strength.

4. The Amp-Side Cable must not be immersed or soaked in fluid of any kind for cleaning purposes.

5. The Amp-Side Cable must be sterilized if it comes into contact with blood or other bodily fluids.

6. The Amp-Side Cable is compatible for use only with the CerebroPatch CSD Detection Array.

7. Whenever there is a risk of contamination, proper cleaning and sterilizing measures must be followed as stated in the Section X. CLEANING and Section XII. STERILIZATION.

8. The CerebroPatch CSD Detection Array must not be autoclaved.

9. U.S. Federal law restricts the use of this device only on the order of a physician or practitioner.

10. Individual CerebroAttach Adhesive Strips must not be used if the sterile pouch has been compromised.

11. The CerebroPatch must not be attached to the scalp using any form of wrapping.

12. If any form of wrapping must be placed over the CerebroPatch, the wrap must be loose enough for two fingers to fit between the device and the wrap.

13. If the CerebroPatch is located on the head of an immobile patient in such a manner as to press into a pillow of the bed, then appropriate head support shall be used to prevent the device from being pushed into the scalp.

V. University of New Mexico Clinical Use

Objectives

The primary objective of this clinical study is to evaluate the effectiveness of the CerebroScope CerebroPatch prototype for detecting CSDs when compared to the established detection method using ECoG electrode strips placed during a surgical procedure in patients with severe brain injury.

Study Design

This study involves three distinct cohorts with five subjects in each cohort. The first cohort consists of normal, healthy volunteers for use as controls to establish baseline data. The second cohort consists of patients with ischemic stroke, subarachnoid hemorrhage, intracranial hemorrhage, or severe traumatic brain injury who had an ECoG strip implanted. This cohort is used for comparing the current standard for detecting cortical spreading depolarization with the CerebroPatch. The third cohort consists of patients with ischemic stroke, subarachnoid hemorrhage, intracranial hemorrhage, or severe traumatic brain injury who have not had an ECoG strip implanted and have not had a craniotomy. All subjects are volunteers recruited at the University of New Mexico or patients in the Neuro-Intensive Care Unit at the University of New Mexico Health Science Center.

Warnings

This Device is only used on human subjects under the approval of the University of New Mexico Institutional Review Board. This study is not designed to prove the safety or efficacy of the CerebroPatch CSD Detection Array. Rather, it is to evaluate the device for proof-of-concept for the noninvasive detection of CSD. This device is not 501(k) approved by the FDA and is for experimental use only at the University of New Mexico Health Sciences Center.

VI. Package Handling

The CerebroPatch and Amp-Side Cable is stored in a cool dry place (10-30° C.). The CerebroPatch has an expiration date and is to be used before the labeled "use by (expiration date)" marked on the label. The sealed pouch is a particulate barrier and does not protect the device from liquids or contaminates. The pouch is not used if it has been compromised. Clean sterile gloves are worn when handling the CerebroPatch.

The CerebroAttach Adhesive Strips are supplied in individual sterile pouches. These individual pouches are provided in quantity, with an expiration date, and are used before the labeled "use by (expiration date)" marked on the pouch. The individual sterile pouch is not to be used if it had been compromised.

VII. Technical Information

The CerebroScope CerebroPatch electrode array is a single-layer thermoplastic elastomer patch using embedded sintered Ag/AgCl electrodes arranged in a hexagonal pattern optimized for the detection and tracking of CSD waves. The electrodes are wired to a multi-pin connector for attachment to the Amp-Side Cable.

The CerebroAttach Adhesive Strip is a medical grade single-layer, double-sided adhesive membrane that is applied to the patch prior to placement on a patient's scalp. This adhesive membrane may remain affixed to the patient for up to 24 hours before requiring replacement of the membrane.

The Amp-Side Cable provides a connection between the multi-pin connector coming from the CerebroPatch and the bio-signal amplifier with 1.5 mm EEG safety DIN connectors.

VIII. Adverse Reactions

Complications which may occur are mild skin irritation, possible skin breakdown, and allergic reaction. In addition, the device may detach during times of profuse sweating.

IX. Operative Techniques

Items which are needed for assembly are: CerebroPatch CSD Detection Array, Amp-Side Cable, CerebroAttach Adhesive Strip, Ten20 Electrode gel, Sterile tongue depressor, Sterile Disposable Drape, Lemon Prep, 2×2 sterile gauze pads, reference and ground electrodes, 70% Isopropyl Alcohol and Sterile water.

When handling the CerebroScope CerebroPatch CSD Detection Array, use of excessive force or high rates of force is to be avoided which could lead to patch rips. The patch is always protected from damage by heavy or sharp objects. To avoid damage or contamination, clean sterile gloves and instruments are used when handling the CerebroScope CerebroPatch.

The Amp-Side Cable is removed from the storage package and inspected for damage. The Amp-Side Cable is connected to the Moberg 40 channel amplifier following the tags on the safety DIN connectors. A sterile work surface is prepared with a sterile disposable surgical drape. The CerebroPatch is removed from the sterilization package and inspected for damage.

As shown in FIG. 10A, the CerebroPatch is placed on the sterile work surface and positioned with electrode holders 34 facing up and a wire harness 48 exiting at the right edge of the device. One sterile pouch is removed containing a CerebroPatch Adhesive Strip from the CerebroAttach box. The sterile pouch is opened and the CerebroAttach Adhesive Strip is removed. The CerebroAttach Adhesive Strip is placed on the sterile work surface. The Adhesive Strip backing is different on each side. The side with a slit is removed first, and this side is placed on the CerebroPatch. The other side has a tab which extends past the edge of the CerebroPatch for ease of removal just prior to placing the device on a patient. Paper backing with the slit is removed from one side of the CerebroAttach Adhesive Strip 50 (FIG. 10B). The CerebroAttach Adhesive Strip is picked up and turned over so that the exposed adhesive is facing down (FIG. 10C). The CerebroAttach Adhesive Strip is attached to the CerebroPatch, matching the outline of the adhesive to the device, and is pushed down lightly to push any air bubbles out from under the tape (FIG. 10D). The remaining length of the CerebroAttach Adhesive Strip is pushed on to the CerebroPatch, pushing down lightly to push any air bubbles out from under the tape. With the CerebroPatch resting on the sterile work surface with the electrode gel reservoirs 36 facing up (FIG. 10E), Ten20 conductive paste 52 is smeared onto the exposed face of the CerebroAttach Adhesive Strip using a sterile tongue depressor and using short circular strokes, scraping gel off of the paper backing and into the depressions at each electrode gel reservoir 36 positions (FIG. 10F). The backing is designed to protect the adhesive layer while allowing the electrode gel reservoirs 36 to be filled. The electrode gel reservoirs 36 are inspected to ensure that each one is completely filled, with no bubbles or gaps in the gel. Once the electrode gel reservoirs 36 are completely filled and only a sheen of gel remains on the paper backing, the other half of the paper backing is removed by pulling up gently on the tab on the CerebroAttach Adhesive Strip (FIG. 10G). The CerebroScope CerebroPatch should be applied to the scalp surface such that the device is directly over and overlapping the ECoG strip according to the physician's or practitioner's previous knowledge.

Prior to device attachment, the skin surface area to be attached to the CerebroPatch and the reference and ground sites are cleaned with a 70% solution of isopropyl alcohol. Following this cleaning, the skin of the patient is prepared with a solution of Lemon Prep. If necessary, remnants of the Lemon Prep are removed by light rubbing with a gauze pad moistened with sterile water.

The assembled and gelled CerebroPatch (FIG. 10H) is attached to the patient's scalp over the prepared skin surface. The CerebroPatch array is pressed down lightly to ensure that the entire surface is engaged with the patient and that no attachment gaps exists between the adhesive portion of the CerebroAttach and skin. Pushing too hard on the tops of the electrode gel reservoirs 36 is to be avoided, as this could force gel out of the cavities and interfere with proper operation of the device. A single electrode is prepared and attached to the patient's ground point or a jumper cable is added to the common ground for other devices. A single electrode is prepared and attached to the preferred reference point. The reference electrode and ground electrode cables are connected to the amplifier. The CerebroPatch connector is attached to the mating connector on the Amp-Side Cable.

The device is removed from the patient at least every 24 hours and the skin of the patient is evaluated for possible deterioration. In such a case, the use of the device is discontinued, temporarily or permanently, or the device is repositioned. After use of the device, it is rinsed with warm water to remove excess gel from the electrodes.

X. Cleaning

The CerebroPatch is cleaned before resterilization and the Amp-Side Cable is cleaned before re-use or sterilization. It should be noted that automated methods or autoclaves must not be used to clean the device.

Pre-Sterilization Cleaning of the CerebroPatch

The device s inspected for any excess gel remaining in the electrode gel reservoirs 36. If gel remains, the device is rinsed under warm water and a cotton swab is used to remove any excess gel. The device is wiped down with enzyme spray (Renuzyme Foam Spray) or enzyme spray followed by immersion in detergent (Enzymatic Detergent Manual Cleaning Concentrate Low Foam).

Post-Use Cleaning of the Amp-Side Cable

The cable is examined for any indications of contamination by blood or bodily fluids. If the cable shows signs of contamination, it is resterilized. If no contaminants are found, the cable is wiped down with a lint free wipe soaked in 70% isopropyl alcohol (IPA). The cable is wrapped and stored in a labeled clean plastic bag for next use.

XI. Sterility

The CerebroScope CerebroPatch and Amp-Side Cable are supplied clean unless the integrity of the package has been compromised. The CerebroScope CerebroPatch and the Amp-Side Cable are supplied unsterile. The CerebroPatch is sterilized prior to attachment to a patient. The Amp-Side Cable is cleaned or sterilized, as above, before use. The CerebroAttach Adhesive Strips are supplied in individual packs which are sterile and do not have to be resterilized prior to use.

XII. Sterilization

Sterilization of the device is done as soon as reasonably practical after use. Resterilized devices remain stored in their sterilization pouches until immediately before use. The CerebroScope CerebroPatch can be sterilized and resterilized a maximum of ten times before compromising the electrical or mechanical properties of the device. It is intended to be sterilized prior to introduction to a new patient. Sterilization is achieved using a standard low-temperature hydrogen peroxide gas plasma sterilization cycle. The CerebroScope CerebroPatch is repackaged in materials appropriate for sterilization.

Due to the tremendous variation in gas sterilization equipment, the choice and validation of specific cycles and aeration parameters are the responsibility of the health care institution. The STERRAD® 100S parameters are as follows: one cycle of Pre-Plasma for ten minutes followed by two cycles with the following parameters: injection for six minutes, diffusion two minutes, and plasma two minutes. After each reprocessing event, the device is visually inspected for any wear or deterioration.

XIII. Disposal

When a CerebroPatch or Amp-Side Cable is no longer usable (more than ten sterilization cycles or damaged), it is returned to CerebroScope.

While the invention has been particularly shown and described with reference to embodiments described above, it will be understood by those skilled in the art that various alterations in form and detail may be made therein without departing from the spirit and scope of the invention, as defined by the appended claims.

What is claimed is:

1. A head-mountable detection device for detecting cortical spreading depression (CSD) in a brain of an individual, comprising:

a plurality of DC-electroencephalogram (DC-EEG) electrodes configured as a high density array of electrodes, each electrode spaced between about 0.5 cm and about 1.5 cm from one another and used to detect CSD non-invasively from a surface of scalp area of the individual, the plurality of DC-EEG electrodes configured to detect real-time DC electrical potential signals, an amplifier unit, wherein the high density array of electrodes is configured to transmit the real-time DC electrical potential signals to the amplifier unit which is configured to amplify the detected DC electrical potential signals, and a computing device comprised of a processing unit which includes one or more processors and a computer-readable memory containing programming instructions which, when executed, cause the processing unit to receive the amplified DC electrical potential signals to implement the programming instructions to produce voltage intensity map images in real time of the DC electrical potential signals and to determine that values of a first set of the DC electrical potential signals corresponding to a first portion of a brain area are depressed which represents a concussion-based CSD, compared to values of a second set of DC electrical potential signals corresponding to a second portion of a brain area which represents normal brain, wherein, in response to the determination that values of the first set are depressed, an output is generated, said output indicating that the individual is experiencing a concussion-based CSD.

2. The head-mountable detection device of claim 1, wherein the electrodes are spaced about 1.0 cm apart from one another.

3. The head-mountable detection device of claim 1, wherein the head-mountable detection device is also configured to detect acute neurological injury- and peri-infarct depolarization (CSD/PID), and CSD associated with migraine auras.

\* \* \* \* \*